(12) United States Patent
Walpin

(10) Patent No.: US 6,458,090 B1
(45) Date of Patent: Oct. 1, 2002

(54) MULTI-POSITIONAL SUPPORT DEVICE

(76) Inventor: Lionel A. Walpin, 127 W. Hazel St., Inglewood, CA (US) 90302

( * ) Notice: Subject to any disclaimer, the term of this patent is extended or adjusted under 35 U.S.C. 154(b) by 0 days.

(21) Appl. No.: 09/565,175

(22) Filed: May 3, 2000

(51) Int. Cl.[7] ................................................. A61F 5/00
(52) U.S. Cl. ................................ 602/18; 128/DIG. 23
(58) Field of Search ...................... 128/845, DIG. 23; 602/17, 18

(56) References Cited

U.S. PATENT DOCUMENTS

| | | | | |
|---|---|---|---|---|
| 2,271,927 A | * | 2/1942 | Saighman | 128/DIG. 23 |
| 2,725,054 A | * | 11/1955 | Harpel | 128/DIG. 23 |
| 2,813,063 A | * | 12/1957 | Smith | 602/18 |
| 3,737,923 A | * | 6/1973 | Prolo | 602/18 |
| 3,810,466 A | * | 5/1974 | Rogers | 128/DIG. 23 |
| 4,099,523 A | * | 7/1978 | Lowrey | 602/16 |
| 4,205,667 A | * | 6/1980 | Gaylord | 602/18 |
| 5,211,623 A | * | 5/1993 | Sarkozi | 602/18 |

* cited by examiner

Primary Examiner—Michael A. Brown
(74) Attorney, Agent, or Firm—Lyon & Lyon LLP

(57) ABSTRACT

A multi-positional support device, one use being to provide the head, neck, and cervical spine of a patient with rest, support, and kinesthetic input in various degrees of head and neck rotation, without causing discomfort to the patient or tilting the patient's head. An embodiment of the present invention comprises an elongate body, a first end, and a second end, said elongate body further comprising a first contoured surface, said first contoured surface comprising a plurality of first surface recesses.

28 Claims, 5 Drawing Sheets

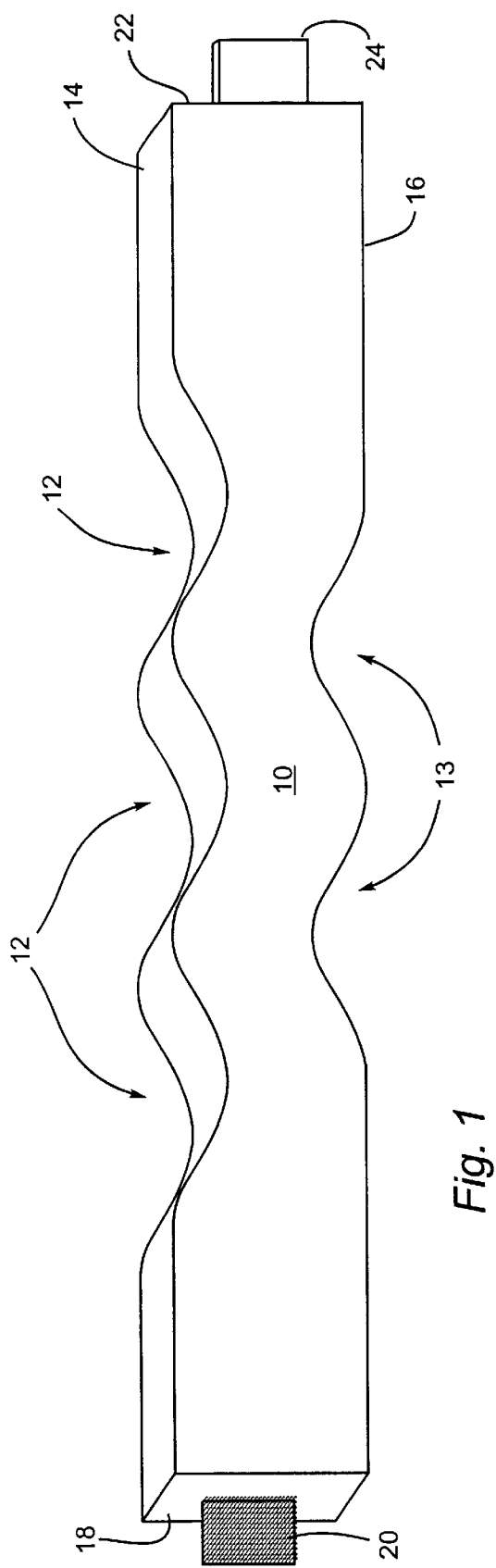
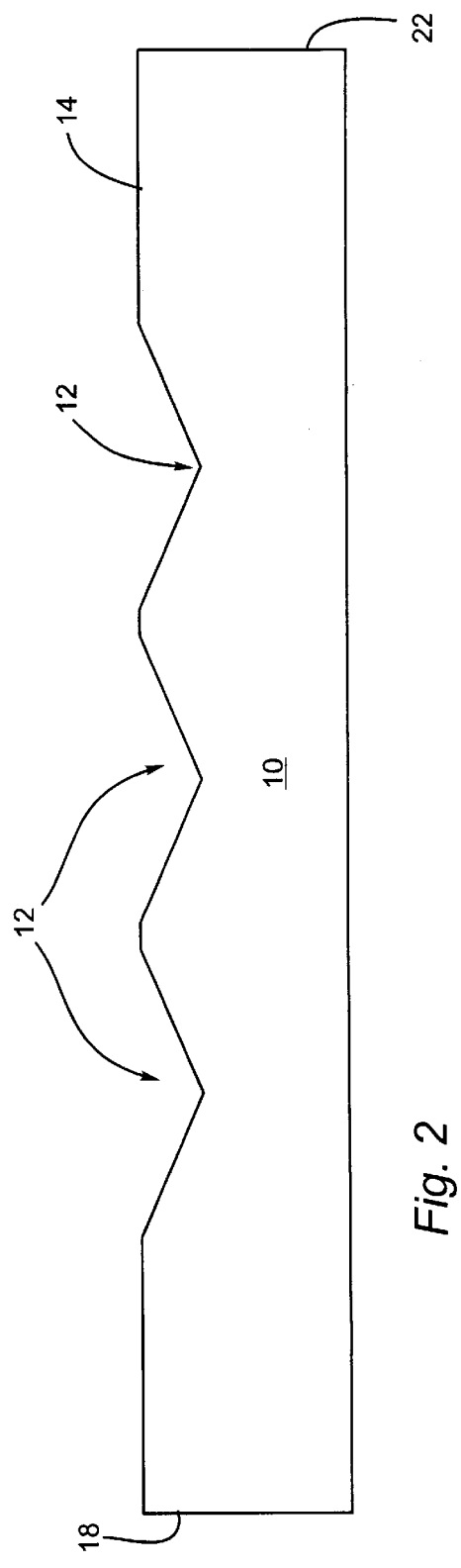
Fig. 1
Fig. 2

MULTI-POSITIONAL SUPPORT DEVICE

FIELD OF THE INVENTION

The invention pertains to the field of orthopedic devices, including, support devices for the head and neck.

BACKGROUND

Known orthopedic devices for use around the neck of a patient are designed to provide support and a degree of comfort for the head, neck, and cervical portion of the spine, hereinafter referred to as the cervical spine. For purposes of this discussion, the cervical spine is not confined anatomically from the C1 to C7 vertebrae. Rather, the cervical spine is also used in the functional sense and includes occiput-C1 through the $3^{rd}$-$4^{th}$ thoracic vertebrae. The cervical spine also includes the related soft tissues, i.e. muscles, ligaments, and connective tissues. These head and neck supports are also designed to provide sensory input for a patient, making a patient more conscious of the postural alignment and position of his or her head and neck. The head and neck supports are soft, semi-rigid, or rigid. There are also rigid braces available to support the head and neck. The majority of these head and neck supports are designed to substantially enclose the neck of a patient, and typically include a recess on the top surface to hold the patient's chin.

Known head and neck supports are generally designed to provide support in the sagittal plane, namely with the patient's head facing straight forward with zero degrees of rotation of the head and/or cervical spine. Although at times this is beneficial during the treatment of disorders including injuries, because the cervical spine is complex anatomically, biomechanically, and functionally, there are also medical conditions whose treatment requires the head and neck to be supported in positions incorporating varying degrees of rotation of the cervical spine.

These effects relate to the complex movements of the anatomical cervical spine comprised of the first cervical vertebrae through the seventh cervical vertebrae. There are facet joints bilaterally between each vertebrae permitting movements of flexion, extension, sidebending, and rotation. Additionally, occipital condyles at the base of the skull articulate with the first cervical vertebrae, permitting the same types of movements. There are also muscles, tendons, ligaments, and connective tissues between all of these structures, and nerve roots exit the spine on each side at each vertebrae. The movements of sidebending and rotation are physiologically combined and in the same direction from the second vertebrae to the seventh vertebrae. Thus, right sidebending and right rotation are combined or linked. Either movement causes the other to also occur together. Contrary to this, the interface between the skull and the first vertebrae allows reversed movements, i.e. linked but to opposite sides. Thus, right rotation of the head on the C1 vertebrae is combined with left sidebending of the head, and vice versa. This reversal of movement explains why we can rotate the head and neck to the right or left and yet have the head remain level, i.e. not tilted. Therefore, if a patient has pain with right sidebending/right rotation of the upper neck, a treatment could be to support it in left sidebending/left rotation. This relieves the right-sided joints and soft tissues from compression and stretches them.

When using known head and neck supports if the neck must be supported in a rotated position, these known devices must be rotated in the desired direction. Because these devices are configured for use in the sagittal plane they are not designed nor intended for use while rotated. Because rotating them often results in a misfit between the patients and the device, the side portions of these devices press upon the patient's head and neck, often imparting an unwanted tilt to the head and resulting in discomfort to the patient. Furthermore, the shape of these devices make the positioning and rotational control of the head and neck less predictable and less achievable. For instance, if a physician determines that a patient's head should be maintained and supported at 15° of left rotation, it is often uncomfortable and difficult to rotate the known head and neck supports so as to actually achieve 15° of head and neck rotation while also keeping the head level, and the patient comfortable. Thus, there is a need for a head and neck support that allows the head and neck to rotate while the device does not. There is also a need for a head and neck support that eliminates the need for the head and neck to literally follow a device that has been rotated. And finally, there is a need for a head and neck support that is able to provide support to a patient at varying, controlled, individual small ranges of head and neck rotation, without causing discomfort or imparting a tilt of the head.

SUMMARY OF THE INVENTION

The present invention comprises a head and neck support device comprising at least one contoured surface. One use of the support device of the present invention is to provide the head, neck, and cervical spine of a patient with rest, support, and kinesthetic input in various degrees of neck rotation, without the need to rotate the support device itself. Rotating a known support device often causes discomfort to the patient, often tilts the patient's head, and does not allow more precise degrees of head and neck rotation.

One embodiment of the head and neck support device of the present invention comprises an elongate body having a first end and a second end, where the elongate body further comprises a first contoured surface having a plurality of first surface recesses. In another embodiment of the present invention, the elongate body further comprises a second contoured surface having a plurality of second surface recesses.

BRIEF DESCRIPTION OF THE DRAWINGS

FIG. 1 illustrates a perspective view of one embodiment of the support device of the present invention.

FIG. 2 illustrates a frontal view of an embodiment of the present invention.

FIG. 3a illustrates a top view of the embodiment of FIG. 2 formed into a ring-like shape as it may be used by a patient.

DETAILED DESCRIPTION OF THE DRAWINGS

Figure 3:
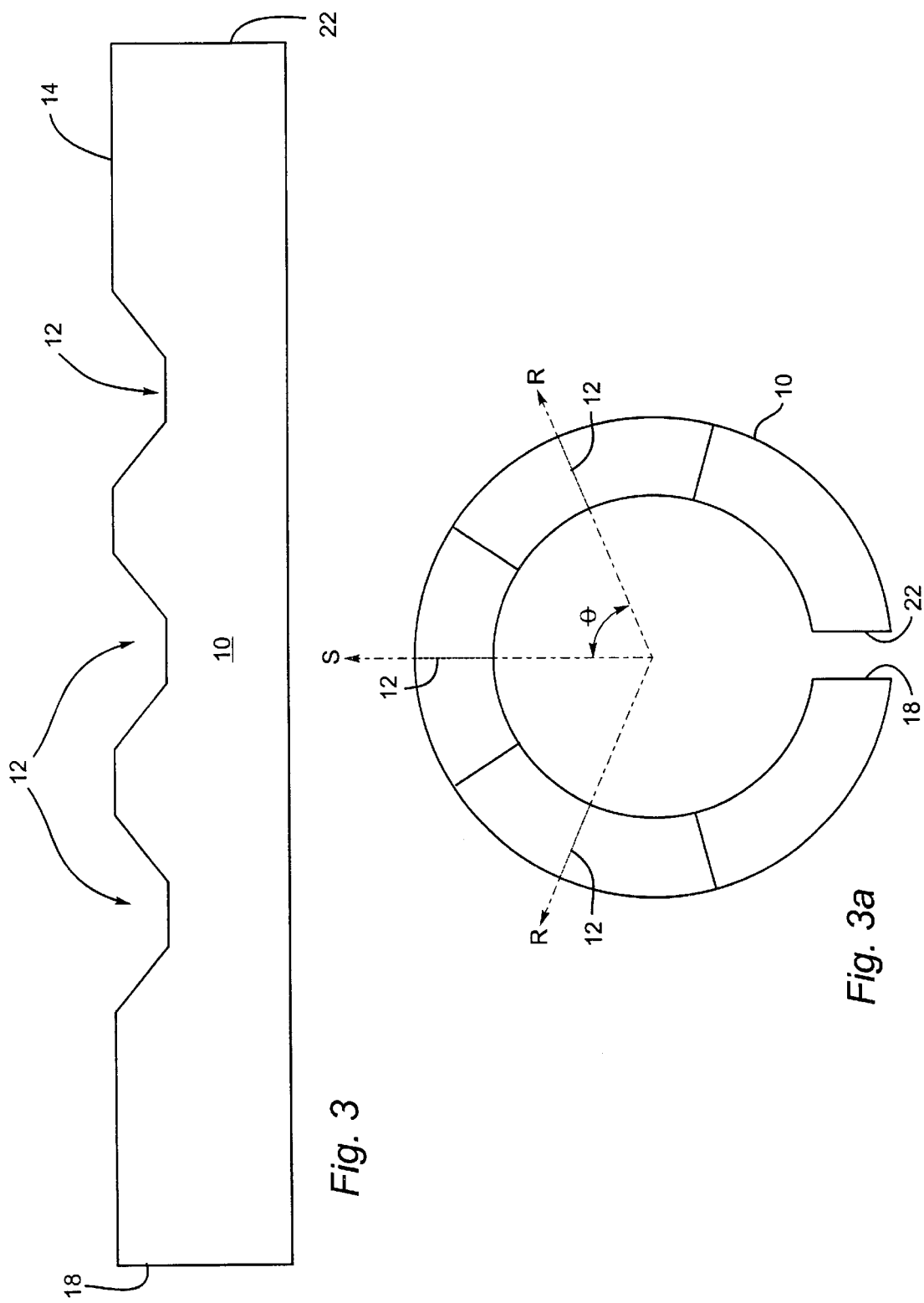
FIG. 3 illustrates a frontal view of another alternate embodiment of the recesses of the present invention.

A preferred embodiment of the present invention comprises a multi-positional support device having an elongate body section. Preferably the elongate body section comprises a first end, a second end, and at least one contoured surface. Preferably the at least one contoured surface has at least two recesses, and the elongate body comprises a flexible material that permits said elongate body to be shaped such that said first end and said second end may be in close proximity to one another.

As seen in FIG. 1, a presently preferred embodiment of the present invention comprises an elongate body 10 having a first contoured surface 14 and a second contoured surface 16. The first contoured surface 14 depicted in FIG. 1 has three first surface recesses 12, and the second contoured surface 16 has two second surface recesses 13. When the elongate body 10 is wrapped around the neck of a patient for use, these recesses 12 and 13 are shaped to retain the chin of the patient. There are a plurality of recesses 12 and 13 on the support device, thereby providing rest, support, and kinesthetic input for the head, neck, and cervical spine of the patient in various degrees of neck rotation.

Preferably, the first surface recesses 12 are located at positions that are offset from the second surface recesses 13. Having the first and second surface recesses offset as depicted in FIG. 1 increases the number of different angles of neck rotation that can be supported with a single support. For example, FIG. 1 depicts a support device having three first surface recesses 12 and two second surface recesses 13 offset from the first surface recesses 12. This results in a total of five different positions in which a chin can be placed to provide five different small ranges of head and neck rotation. Three individual small ranges of head and neck rotation are provided by the first surface recesses 12 when the first contoured surface 14 is the top surface when used by a patient, and two additional individual small ranges of head and neck rotation are provided by the second surface recesses 13 when the support device is flipped over so that the second contoured surface 16 is the top surface when used by a patient. It should be noted that for ease in describing the invention, use of the term "top surface" shall refer to the surface adjacent to the chin of a patient (i.e. the surface that the chin is resting upon) when the support is being used by a patient. Thus, the center recess of the first contoured surface 14 allows the chin to rest in the sagittal plane (zero degrees of rotation), and the remaining recesses 12 and 13 allow the head and neck to be supported in varying degrees of left and right neck rotation.

The recesses 12 and 13 are designed to be deep enough to support and retain the chin of a patient comfortably. It is preferred that the depth of the recesses be between one-eighth of an inch to one inch deep. Although they preferably have a rounded or curved contour, they may be formed in any shape that will comfortably retain the chin of a patient as illustrated by the frontal views of alternate embodiments of the present invention in FIGS. 2 and 3. FIG. 2 depicts an embodiment having a first contoured surface 14 with recesses 12 that are angular, similar to triangular cut-outs. And FIG. 3 depicts an embodiment with a first contoured surface 14 having recesses 12 that are gear-tooth shaped, similar to trapezoidal cut-outs. The recesses may also be custom-made to the specific contours of the chin of a patient to provide maximum comfort and support. It should also be noted that as shown in FIGS. 2 and 3, in an alternate embodiment the elongate body may only comprise a single contoured surface 14.

Turning to FIG. 3a, the embodiment of FIG. 2 is again shown with the support device formed into a substantially ring-like shape, as it typically would be when used by a patient. In this drawing, the lowest portions of the recesses 12 are shown by the dashed lines, and the peaks in between each recess 12 are shown by the solid lines. The support device is typically oriented such that the first end 18 and second end 22 of the elongate body 10 will meet at the back of a patient's neck. In accordance with this orientation, axis S represents the sagittal plane or an angle of zero degrees. Thus a patient who requires head and neck support while facing straight forward will utilize the recess 12 that lies along axis S. And axis R represents a rotated plane or an angle of θ, measured from the sagittal plane.

The support device of the present invention preferably further comprises a fastener for holding the first and second ends 18 and 22 together. An example of a fastener that may be used is a Velcro® type fastener with one portion 20 attached to end 18 and the second portion 24 attached to end 22. The portions 20 and 24 can be of any type that adequately holds the ends 18 and 22 of the elongate body 10 together when the support device is wrapped around the neck of a patient. Snaps, buttons, strings, or any other type of fastener may also be used. The fastener portions 20 and 24 can be located on the ends 18 and 22, or they can be located on the front surface of the elongate body 10 towards the ends 18 and 22. It is presently preferred that the fasteners 20 and 24 be removable so that the ends 18 and 22 of the elongate body 10 may be trimmed to conform to the circumference of a patient's neck.

In lieu of the fastener portions 20 and 24, the ends 18 and 22 may be configured such that they interlock and stay joined without the need for fasteners. The ends 18 and 22 may be designed as a tab and slot, a tongue and groove, or a key and lock so that they can be coupled together. For example, end 18 may comprise a "T" shaped tab, and end 22 may comprise a "T" shaped slot, so that the end 18 fits into the end 22 to hold the ends of the support device together. Alternately, end 18 may comprise a long tab and end 22 may comprise a slot. The ends are coupled by inserting the tab of end 18 into the slot of end 22. In such an embodiment, the tab 18 may be trimmable to allow the patient to conform the support device to the circumference of their neck.

The elongate body 10 is preferably constructed from a flexible polyurethane foam. In an alternate embodiments, other materials may be used such as semi-rigid or rigid foam, other types of flexible foam, or even metal. The thickness of the material used to fabricate the elongate body 10 may also vary based on a patient's needs, although the thickness of the support device preferably ranges from a quarter of an inch to two inches in thickness. Similarly, the height of the device may vary based on the patient, although it preferably ranges from one inch to seven inches in height.

The support device of the present invention preferably further comprises a cover (not shown) for the elongate body 10. The cover is preferably made of fabric, but any number of materials may be used. The cover provides additional comfort for the patient when using the support device of the present invention. The fastener may attach to the cover in certain embodiments instead of directly to the ends of the elongate body 10.

Figure 4:
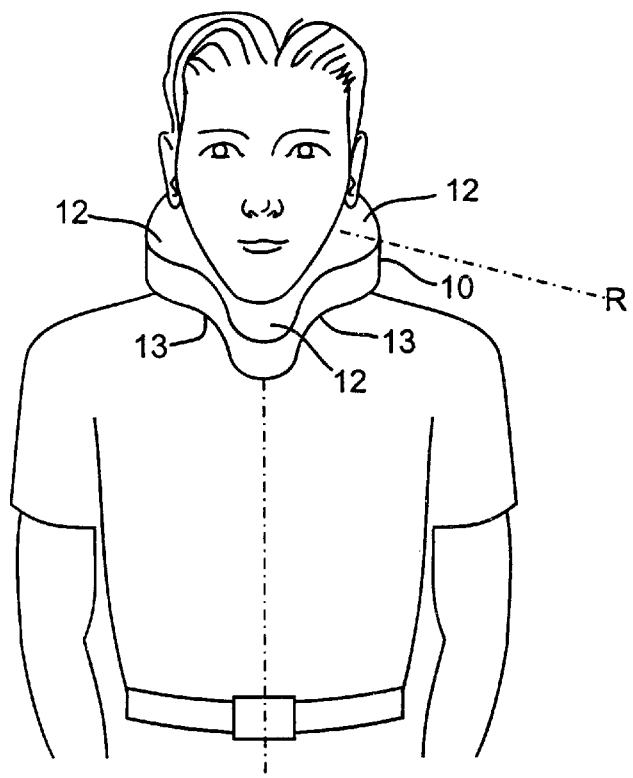
FIG. 4 depicts one embodiment of the present invention in use on a patient with the head and neck supported in the sagittal plane.
Figure 5:
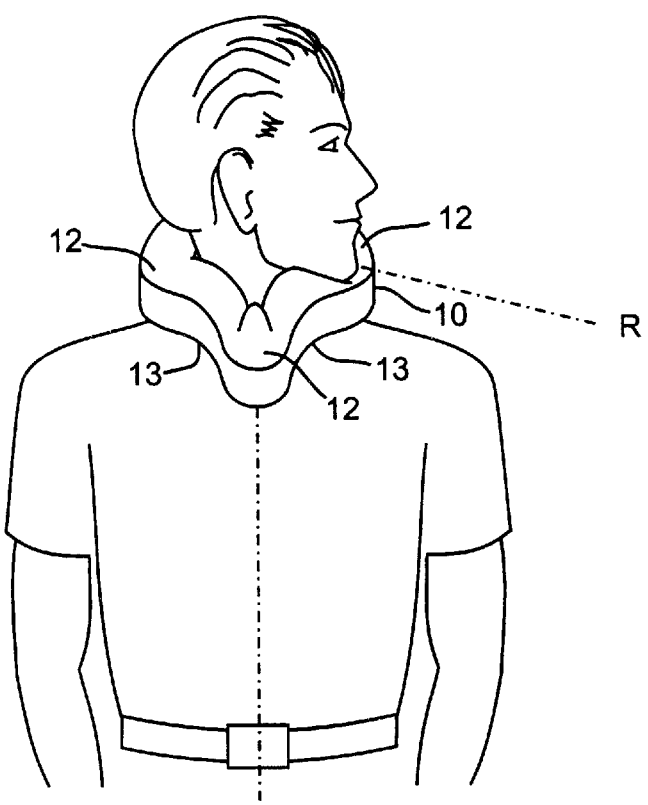
FIG. 5 depicts one embodiment of the present invention by a patient with the head and neck supported in a rotated plane.

FIG. 4 shows an embodiment of the support device of the present invention as used by a patient with his head being supported in the sagittal plane, defined by axis S. FIG. 5 illustrates the same patient using the same embodiment as shown in FIG. 4 where the head and neck are supported in a position and alignment that are rotated, defined by axis R. The orientation of the support device relative to the body has not changed from FIG. 4 to FIG. 5. The recesses on the contoured surfaces of the present invention can be precisely located allowing small individual ranges of neck rotation to provide the most benefit in a consistent manner. This feature of the present invention eliminates the unwanted tilting of the head and neck and the uncomfortable pressures on the head and neck that are caused by known head and neck supports when they are rotated.

Figure 6:
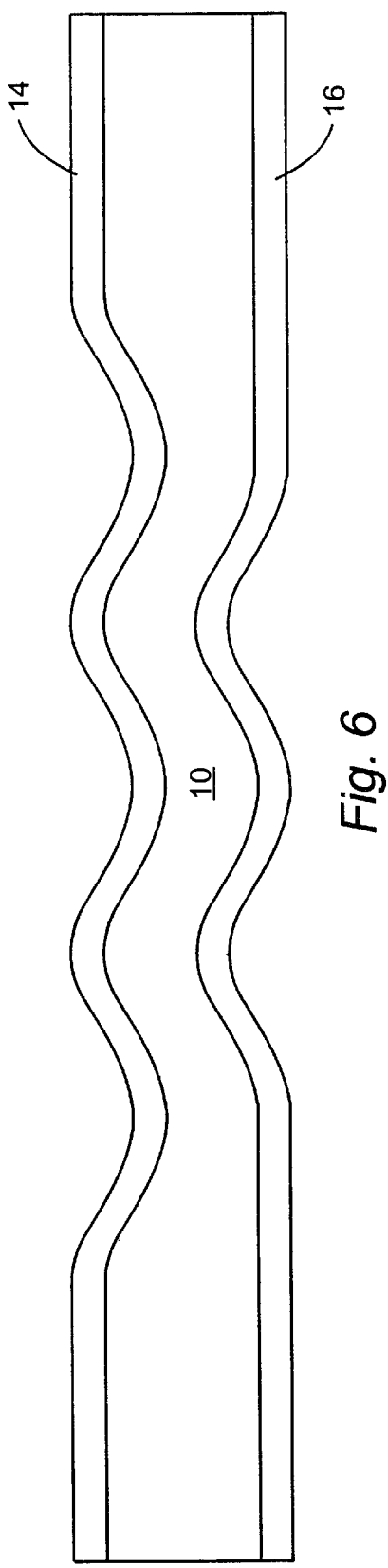
FIG. 6 illustrates a frontal view of an alternate embodiment of the present invention where the first and second contoured surfaces comprise a different material than the elongate core.

Turning to FIG. 6, in an alternate embodiment of the present invention, the first contoured surface 14 and the second contoured surface 16 of the present invention comprise layers formed of a different material than elongate body 10 itself. For example, the first contoured surface 14 and the second contoured surface 16 may comprise a viscoelastic memory foam to provide even greater comfort to a patient.

Figure 7:
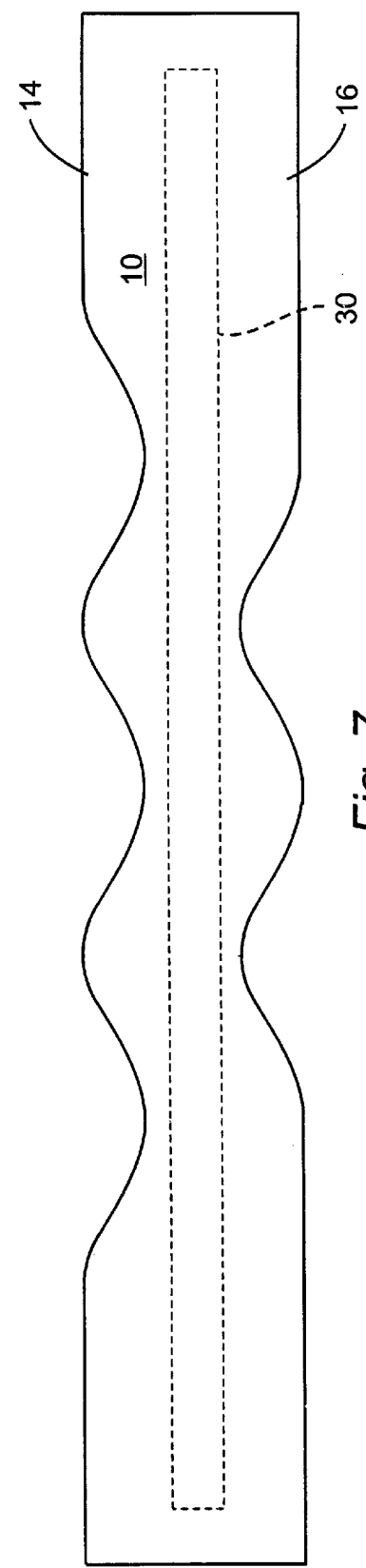
FIG. 7 illustrates a frontal view of an alternate embodiment of the present invention where an inner core is located within the elongate body to provide additional support.

As seen in FIG. 7, in another alternate embodiment the elongate body may further comprise an inner core 30 to provide additional support. This inner core 30 may comprise any material known to be useful for adding support, such as a material that is relatively more rigid than the foam used in the elongate body, or a flexible memory retaining material such as aluminum or a malleable metal. Alternatively, the inner core 30 may comprise an inflatable bladder containing air or water that can provide a varying amount of support depending upon the amount of air or water added.

Figure 8:
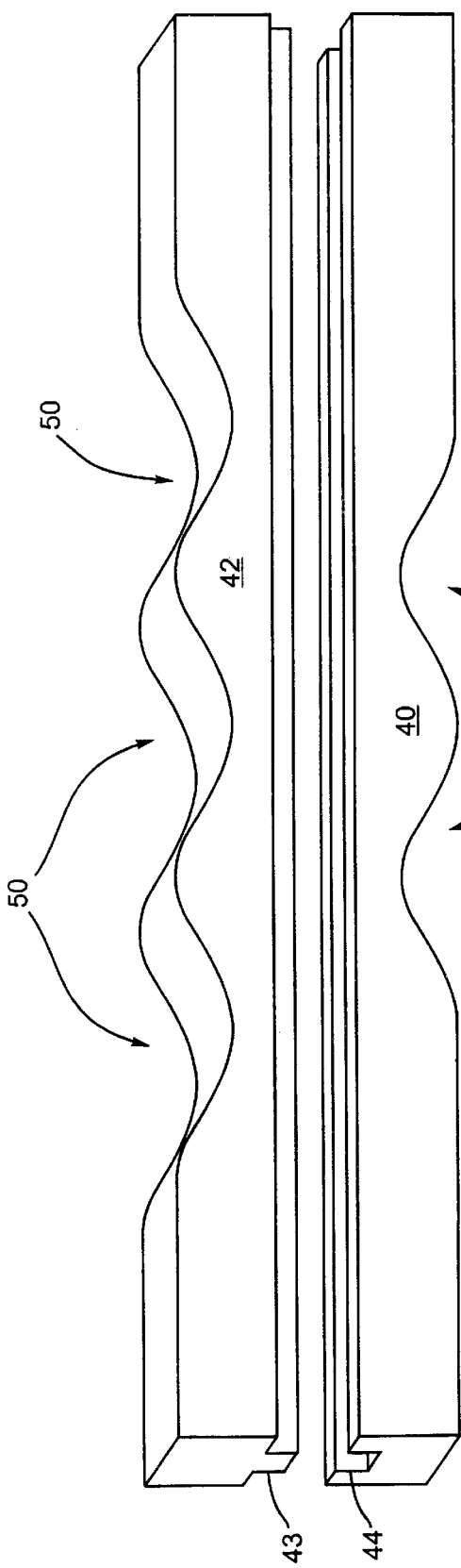
FIG. 8 illustrates a perspective view of one alternative embodiment of the present invention where the support device comprises two halves that are coupled so that they can slide with respect to each other.

FIG. 8 illustrates another embodiment of the present invention. The support device of this embodiment comprises a male elongate body 42 and a female elongate body 40. Both the male and the female elongate bodies comprise a contoured surface with one or more recesses 50. Male elongate body 42 further comprises a lengthwise tongue 43, while female elongate body 40 further comprises a lengthwise groove 44. The tongue 43 fits into groove 44 to enable the two elongate bodies to be slidably joined so that the two may slide longitudinally with respect to one another.

Figure 9:
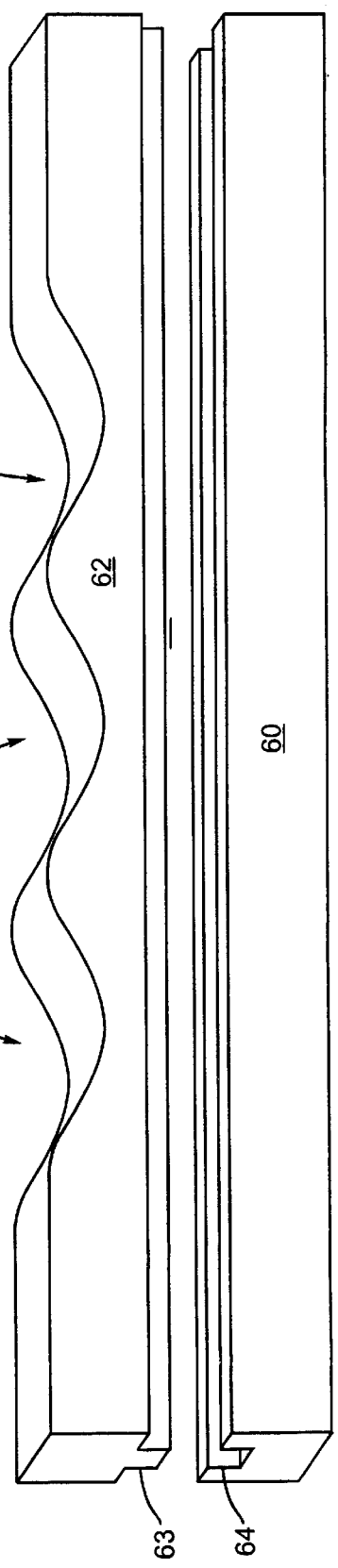
FIG. 9 illustrates a perspective view of another alternative embodiment of the present invention where the support device comprises a base with a sliding chin support.

FIG. 9 illustrates yet another alternate embodiment of the present invention. Here, the support device comprises an elongate base 60 with a sliding chin support 62 located on a top surface 61 of the elongate base 60. The chin support 62 can slide back and forth along the top surface 61 in this embodiment, utilizing some form of sliding mechanism. In the illustrated embodiment, the sliding mechanism is in the form of a tongue 63 and groove 64. The chin support 62 has the tongue 63 which is located on its bottom surface, and the elongate base 60 has the groove 64 into which the tongue 63 is inserted. The groove 64 preferably extends along substantially the entire length of the elongate base 60. The chin support 62 may now slide back and forth along the top surface 61 within the groove 64. One or more chin receptacles 65 are located in the chin support 62 to provide places for a patient's chin to rest within. In this embodiment, the various degrees of neck rotation are achieved by sliding the chin support 62 along the top surface 61 to place a chin receptacle 65 in a desired location. A mechanism such as a lock may be provided to securely secure the chin support 62 in place once it has been adjusted.

One method of using the head and neck support device of the present invention is to place the elongate body 10 around the neck of a patient oriented with the first and second ends 18 and 22 meeting at the back of the patient's neck, such that the interface where the ends 18 and 22 meet is substantially aligned with the sagittal plane. The chin of the patient is then positioned within one of the recesses. Preferably, a fastener is used to fasten the ends 18 and 22 together to hold the support device around the neck of the patient. Now, if the patient needs to reposition his or her head and neck to support them at a different angle, the patient can reposition his or her chin within another recess on the top contoured surface without removing or reorienting the support device.

In the event that the patient needs to reposition his or her head and neck at an angle that is not provided for by the recesses in the top contoured surface, the patient may remove the support device and flip the support device over so that the former bottom contoured surface is the new top contoured surface. The recesses on the new top contoured surface are at different positions than the recesses on the former top contoured surface, thus providing angles that the former top contoured surface could not provide. The support device is then replaced around the neck of the patient so that the first and second ends 18 and 22 again meet at the back of the patient's neck such that the interface where the ends 18 and 22 meet is substantially aligned with the sagittal plane, and the chin of the patient is again positioned within one of the recesses located on the new top contoured surface.

Another method of use is when a patient using the support device desires to remove it for a duration of time. Here, the elongate body 10 is first placed around the neck of a patient oriented with the first and second ends 18 and 22 meeting at the back of the patient's neck, such that the interface where the ends 18 and 22 meet is substantially aligned with the sagittal plane. Next, the chin of the patient is positioned within one of the recesses. At some point thereafter, the patient may remove the device for a duration of time. Subsequently when the patient wishes to again use the support device, the elongate body 10 is replaced around the neck of a patient oriented with the first and second ends 18 and 22 meeting at the back of the patient's neck, such that the interface where the ends 18 and 22 meet is again substantially aligned with the sagittal plane. This ensures that the recesses will be positioned at the same locations as before. Finally, the chin of the patient is again positioned within one of the recesses.

Thus, a head and neck support device and methods of its use have been described. While embodiments, applications, and advantages of the invention have been shown and described, many more embodiments and advantages are possible without deviating from the inventive concepts described herein. Thus, the invention is not to be restricted except in accordance with the spirit of the appended claims.

What is claimed is:

1. A support, comprising:
    an elongate body, said elongate body further comprising:
        a first contoured surface, said first contoured surface comprising a plurality of first surface recesses for chin support,
        a first end, and
        a second end.

2. The support of claim 1, further comprising a second contoured surface, said second contoured surface comprising a plurality of second surface recesses for chin support.

3. The support of claim 2, wherein said first surface recesses are located at positions offset from said second surface recesses.

4. The support of claim 1, further comprising a fastener, a first portion of said fastener attached to said first end and a second portion of said fastener attached to said second end.

5. The support of claim 4, wherein said fastener comprises a Velcro closure.

6. The support of claim 1, wherein said elongate body comprises a flexible visco-elastic foam.

7. The support of claim 1, further comprising a fastener, a first portion of said fastener attached to a frontal surface of said elongate body in close proximity to said first end, and a second portion of said fastener attached to said frontal surface of said elongate body in close proximity to said second end.

8. The support of claim 5, wherein said fastener comprises a hook and loop material.

9. The support of claim 7, wherein said fastener comprises a snap-button closure.

10. The support of claim 1, wherein said elongate body further comprises an inner core to provide support.

11. The support of claim 10, wherein said inner core comprises a bladder containing air.

12. The multi-positional collar of claim 10, wherein said inner core comprises a bladder containing water.

13. The support of claim 1, wherein said elongate body comprises a plurality of materials.

14. The support of claim 4, wherein said fastener comprises a hook and loop material.

15. The support of claim 1, further comprising a cover for said elongate body.

16. A support, comprising:
   an elongate base, said elongate base comprising a top surface, a first end, and a second end; and
   a chin support, said chin support further comprising one or more chin receptacles, said chin support slidably coupled to said elongate base such that said chin support can slide back and forth along said top surface to accommodate various degrees of neck rotation.

17. The support of claim 15, further comprising a fastener, a first portion of said fastener attached to said cover in close proximity to said first end, and a second portion of said fastener attached to said cover in close proximity to said second end.

18. A support, comprising:
   an elongate base, said elongate base comprising a top surface, a first end, and a second end;
   a chin support, said chin support further comprising one or more chin receptacles, said chin support slidably coupled to said elongate base such that said chin support can slide back and forth along said top surface to accommodate various degrees of neck rotation; and
   a fastener, said fastener having a first portion attached to a frontal surface of said elongate base in close proximity to said first end, and a second portion of said fastener attached to said frontal surface of said elongate base in close proximity to said second end.

19. A support, comprising:
   an elongate base, said elongate base comprising a top surface, a first end, and a second end; and
   a chin support, said chin support further comprising one or more chin receptacles, said chin support slidably coupled to said elongate base such that said chin support can slide back and forth along said top surface to accommodate various degrees of neck rotation, said chin support further comprising visco-elastic foam.

20. A support, comprising:
   an elongate base, said elongate base comprising a top surface, a first end, and a second end, said elongate base further comprising a flexible polyurethane foam; and
   a chin support, said chin support further comprising one or more chin receptacles, said chin support slidably coupled to said elongate base such that said chin support can slide back and forth along said top surface to accommodate various degrees of neck rotation.

21. A support, comprising:
   an elongate base, said elongate base comprising a top surface, a first end, and a second end; and
   a chin support, said chin support further comprising one or more chin receptacles, said chin support slidably coupled to said elongate base such that said chin support can slide back and forth along said top surface to accommodate various degrees of neck rotation, said chin support further comprising a flexible polyurethane foam.

22. A support, comprising:
   an elongate base, said elongate base comprising a top surface, a first end, and a second end; and
   a chin support, said chin support further comprising one or more chin receptacles, said chin support slidably coupled to said elongate base such that said chin support can slide back and forth along said top surface to accommodate various degrees of neck rotation; and
   a cover for said elongate base.

23. The support of claim 22, said cover further comprising fabric.

24. A support, comprising:
   an elongate base, said elongate base comprising a top surface, a first end, and a second end;
   a chin support, said chin support further comprising one or more chin receptacles, said chin support slidably coupled to said elongate base such that said chin support can slide back and forth along said top surface to accommodate various degrees of neck rotation; and
   a lock to hold said chin support in place.

25. A support, comprising:
   a male elongate core, said male elongate core comprising a first contoured surface, said first contoured surface comprising a plurality of first surface recesses, and said first elongate core further comprising a tongue;
   a female elongate core, said female elongate core comprising a second contoured surface, said second contoured surface comprising a plurality of second surface recesses, and said second elongate core further comprising a groove;
   wherein said tongue of said male elongate core is located within said groove of said female elongate core such that both elongate cores are coupled and can slide back and forth with respect to each other.

26. A method of using a support, said support comprising:
   an elongate body, said elongate body further comprising:
      a first contoured surface, said first contoured surface comprising a plurality of first surface recesses for chin support,
      a first end, and
      a second end;
   said method comprising:
      placing said support around a neck of a user such that said first end and said second end are in close proximity to one another;
      positioning a chin of said user within one of said first surface recesses located on said first contoured surface; and
      without removing said support, repositioning said chin within another of said first surface recesses in said first contoured surface.

27. A method of using a support, said support comprising:

an elongate body, said elongate body further comprising:
- a first contoured surface, said first contoured surface comprising a plurality of first surface recesses for chin support,
- a first end, and
- a second end;

said method comprising:
- placing said support around a neck of a user such that said first end and said second end are in close proximity to one another;
- positioning a chin of said user within one of said first surface recesses located on said first contoured surface; and
- without reorienting said support, repositioning said chin within another of said first surface recesses in said first contoured surface.

28. A method of using a support, said support comprising:

an elongate body, said elongate body further comprising:
- a first contoured surface, said first contoured surface comprising a plurality of first surface recesses for chin support,
- a second contoured surface, said second contoured surface comprising a plurality of second surface recesses for chin support,
- a first end, and
- a second end;

said method comprising:
- placing said support around a neck of a user such that said first contoured surface is adjacent to a chin of said user, and said first end and said second end are in close proximity to one another;
- positioning said chin within one of said first surface recesses located on said first contoured surface;
- removing the support;
- re-placing the support around said neck of said user such that said second contoured surface is adjacent to said chin of said user, and said first end and said second end are in close proximity to one another and are located in substantially the same location relative to said neck as before; and
- positioning said chin within one of said second surface recesses located on said second contoured surface.

* * * * *